(12) United States Patent
Vaughan et al.

(10) Patent No.: US 7,736,374 B2
(45) Date of Patent: Jun. 15, 2010

(54) TISSUE MANIPULATION AND SECUREMENT SYSTEM

(75) Inventors: Robert A. Vaughan, Laguna Niguel, CA (US); Cang C. Lam, Irvine, CA (US); Richard C. Ewers, Fullerton, CA (US); Vahid Saadat, Saratoga, CA (US)

(73) Assignee: USGI Medical, Inc., San Clemente, CA (US)

(*) Notice: Subject to any disclaimer, the term of this patent is extended or adjusted under 35 U.S.C. 154(b) by 318 days.

(21) Appl. No.: 11/070,846

(22) Filed: Mar. 1, 2005

(65) Prior Publication Data

US 2005/0251165 A1    Nov. 10, 2005

(51) Int. Cl.
*A61B 17/08* (2006.01)
*A61B 17/12* (2006.01)
*A61B 17/00* (2006.01)

(52) U.S. Cl. .................... 606/153; 606/144; 606/205

(58) Field of Classification Search ................. 606/153, 606/205–208, 144
See application file for complete search history.

(56) References Cited

U.S. PATENT DOCUMENTS

| | | | |
|---|---|---|---|
| 2,201,610 A | 5/1940 | Dawson, Jr. |
| 2,413,142 A | 12/1946 | Jones et al. |
| 3,150,379 A | 9/1964 | Brown |
| 3,166,072 A | 1/1965 | Sullivan, Jr. |
| 3,494,006 A | 2/1970 | Brumlik |
| 3,551,987 A | 1/1971 | Wilkinson |
| 3,646,615 A | 3/1972 | Ness |
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,915,157 A | 10/1975 | Mitsui |

(Continued)

FOREIGN PATENT DOCUMENTS

EP    0 480 428 A2    4/1992

(Continued)

OTHER PUBLICATIONS

Angiolink, The Expanding Vascular Staple [brochure], date unknown, 1 page total.

(Continued)

*Primary Examiner*—Todd E Manahan
*Assistant Examiner*—Diane Yabut
(74) *Attorney, Agent, or Firm*—Levine Bagade Han LLP; Charles C. Fowler

(57) ABSTRACT

Tissue manipulation and securement systems are described herein. A tissue manipulation assembly is pivotably coupled to the distal end of a tubular member and has a lower jaw member and an upper jaw member pivotably coupled to the lower jaw member. A reconfigurable launch tube is also pivotably coupled to the upper jaw member and is used to urge the jaw members from a low-profile configuration to an open configuration for receiving tissue. The tissue manipulation assembly may be advanced through a shape-lockable endoscopic device, a conventional endoscope, or directly by itself into a patient. A second tool can be used in combination with the tissue manipulation assembly to engage tissue and manipulate the tissue in conjunction with the tissue manipulation assembly.

21 Claims, 12 Drawing Sheets

U.S. PATENT DOCUMENTS

| | | |
|---|---|---|
| 3,976,079 A | 8/1976 | Samuels et al. |
| 4,007,743 A | 2/1977 | Blake |
| 4,060,089 A | 11/1977 | Noiles |
| 4,069,825 A | 1/1978 | Akiyama |
| 4,245,624 A | 1/1981 | Komiya |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,763,669 A * | 8/1988 | Jaeger ................... 600/564 |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsh et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,254,126 A | 10/1993 | Filipi et al. |
| 5,261,916 A | 11/1993 | Engelson |
| 5,268,001 A | 12/1993 | Nicholson et al. |
| 5,269,809 A * | 12/1993 | Hayhurst et al. ............ 606/232 |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,342,376 A | 8/1994 | Ruff |
| 5,345,949 A | 9/1994 | Shlain |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst et al. |
| 5,417,699 A | 5/1995 | Klein et al. |
| 5,423,854 A * | 6/1995 | Martin et al. ................ 606/205 |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,582,617 A * | 12/1996 | Klieman et al. ............. 606/170 |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,662 A | 9/1997 | Bishop et al. |
| 5,662,663 A | 9/1997 | Shallman |

| Patent No. | Date | Name |
|---|---|---|
| 5,665,109 A | 9/1997 | Yoon |
| 5,665,112 A | 9/1997 | Thal |
| 5,667,513 A | 9/1997 | Torrie et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,421 A | 12/1997 | Schneidt |
| 5,707,394 A | 1/1998 | Miller et al. |
| 5,709,708 A | 1/1998 | Thal |
| 5,713,903 A | 2/1998 | Sander et al. |
| 5,720,765 A | 2/1998 | Thal |
| 5,724,978 A | 3/1998 | Tenhoff |
| 5,725,552 A | 3/1998 | Kotula et al. |
| 5,732,707 A | 3/1998 | Widder et al. |
| 5,741,297 A | 4/1998 | Simon |
| 5,749,893 A | 5/1998 | Vidal et al. |
| 5,752,963 A | 5/1998 | Allard et al. |
| 5,766,189 A | 6/1998 | Matsuno |
| 5,766,196 A * | 6/1998 | Griffiths .................. 606/170 |
| 5,779,719 A | 7/1998 | Klein et al. |
| 5,782,859 A | 7/1998 | Nicholas et al. |
| 5,782,865 A | 7/1998 | Grotz |
| 5,787,897 A | 8/1998 | Kieturakis |
| 5,792,152 A | 8/1998 | Klein et al. |
| 5,792,153 A | 8/1998 | Swain et al. |
| 5,797,929 A | 8/1998 | Andreas et al. |
| 5,797,960 A | 8/1998 | Stevens et al. |
| 5,810,849 A | 9/1998 | Kontos |
| 5,810,851 A | 9/1998 | Yoon |
| 5,810,853 A | 9/1998 | Yoon |
| 5,810,879 A | 9/1998 | de Guillebon |
| 5,814,070 A | 9/1998 | Borzone et al. |
| 5,817,110 A | 10/1998 | Kronner |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,846,261 A | 12/1998 | Kotula et al. |
| 5,855,614 A | 1/1999 | Stevens et al. |
| 5,860,991 A | 1/1999 | Klein et al. |
| 5,861,003 A | 1/1999 | Latson et al. |
| 5,868,762 A | 2/1999 | Cragg et al. |
| 5,879,371 A | 3/1999 | Gardiner et al. |
| 5,887,594 A | 3/1999 | LoCicero, III |
| 5,888,247 A | 3/1999 | Benetti |
| 5,891,168 A | 4/1999 | Thal |
| 5,893,856 A | 4/1999 | Jacobs et al. |
| 5,895,404 A | 4/1999 | Ruiz |
| 5,897,562 A | 4/1999 | Bolanos et al. |
| 5,899,914 A * | 5/1999 | Zirps et al. ................ 606/170 |
| 5,899,920 A | 5/1999 | DeSatnick et al. |
| 5,899,921 A | 5/1999 | Caspari et al. |
| 5,901,895 A | 5/1999 | Heaton et al. |
| 5,916,224 A | 6/1999 | Esplin |
| 5,925,059 A | 7/1999 | Palermo et al. |
| 5,928,264 A | 7/1999 | Sugarbaker et al. |
| 5,944,738 A | 8/1999 | Amplatz et al. |
| 5,947,983 A | 9/1999 | Solar et al. |
| 5,947,997 A | 9/1999 | Pavcnik et al. |
| 5,948,001 A | 9/1999 | Larsen |
| 5,954,731 A | 9/1999 | Yoon |
| 5,954,732 A | 9/1999 | Hart et al. |
| 5,961,440 A | 10/1999 | Schweich, Jr. et al. |
| 5,964,765 A | 10/1999 | Fenton, Jr. et al. |
| 5,964,782 A | 10/1999 | Lafontaine et al. |
| 5,964,783 A | 10/1999 | Grafton et al. |
| 5,976,073 A | 11/1999 | Ouchi |
| 5,976,127 A | 11/1999 | Lax |
| 5,976,158 A | 11/1999 | Adams et al. |
| 5,976,159 A | 11/1999 | Bolduc et al. |
| 5,980,558 A | 11/1999 | Wiley |
| 5,984,933 A | 11/1999 | Yoon |
| 5,993,476 A | 11/1999 | Groiso |
| 6,013,083 A | 1/2000 | Bennett |
| 6,017,358 A | 1/2000 | Yoon et al. |
| 6,027,523 A | 2/2000 | Schmieding |
| 6,033,430 A | 3/2000 | Bonutti |
| 6,045,497 A | 4/2000 | Schweich, Jr. et al. |
| 6,045,573 A | 4/2000 | Wenstrom, Jr. et al. |
| 6,050,936 A | 4/2000 | Schweich, Jr. et al. |
| 6,053,935 A | 4/2000 | Brenneman et al. |
| 6,059,715 A | 5/2000 | Schweich, Jr. et al. |
| 6,059,719 A | 5/2000 | Yamamoto et al. |
| 6,074,401 A | 6/2000 | Gardiner et al. |
| 6,077,214 A | 6/2000 | Mortier et al. |
| 6,077,281 A | 6/2000 | Das |
| 6,077,291 A | 6/2000 | Das |
| 6,079,414 A | 6/2000 | Roth et al. |
| 6,086,600 A | 7/2000 | Kortenbach |
| 6,086,601 A | 7/2000 | Yoon |
| 6,110,183 A | 8/2000 | Cope |
| 6,113,609 A | 9/2000 | Adams et al. |
| 6,113,611 A | 9/2000 | Allen et al. |
| 6,119,913 A | 9/2000 | Adams et al. |
| 6,149,658 A | 11/2000 | Gardiner et al. |
| 6,152,935 A | 11/2000 | Kammerer et al. |
| 6,159,146 A | 12/2000 | El Gazayerli |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,167,889 B1 | 1/2001 | Benetti |
| 6,171,320 B1 | 1/2001 | Monassevitch |
| 6,174,323 B1 | 1/2001 | Biggs et al. |
| 6,179,195 B1 | 1/2001 | Adams et al. |
| 6,183,411 B1 | 2/2001 | Mortier et al. |
| RE37,117 E | 3/2001 | Palermo |
| 6,197,022 B1 | 3/2001 | Baker |
| 6,214,007 B1 | 4/2001 | Anderson |
| 6,231,561 B1 | 5/2001 | Frazier et al. |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,270,515 B1 | 8/2001 | Linden et al. |
| 6,283,973 B1 | 9/2001 | Hubbard et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,312,437 B1 | 11/2001 | Kortenbach |
| 6,315,789 B1 | 11/2001 | Cragg |
| 6,322,563 B1 | 11/2001 | Cummings et al. |
| 6,322,580 B1 | 11/2001 | Kanner |
| 6,332,468 B1 | 12/2001 | Benetti |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,352,503 B1 | 3/2002 | Matsui et al. |
| 6,355,052 B1 | 3/2002 | Neuss et al. |
| 6,358,197 B1 | 3/2002 | Silverman et al. |
| 6,363,938 B2 | 4/2002 | Saadat et al. |
| 6,368,339 B1 | 4/2002 | Amplatz et al. |
| 6,387,104 B1 | 5/2002 | Pugsley, Jr. et al. |
| 6,394,949 B1 | 5/2002 | Crowley et al. |
| 6,402,679 B1 | 6/2002 | Mortier et al. |
| 6,402,680 B2 | 6/2002 | Mortier et al. |

| Patent Number | Date | Inventor |
|---|---|---|
| 6,406,420 B1 | 6/2002 | McCarthy et al. |
| H2037 H | 7/2002 | Yates et al. |
| 6,423,087 B1 | 7/2002 | Sawada |
| 6,425,911 B1 | 7/2002 | Akerfeldt et al. |
| 6,447,533 B1 | 9/2002 | Adams et al. |
| 6,494,888 B1 | 12/2002 | Laufer et al. |
| 6,506,196 B1 | 1/2003 | Laufer |
| 6,533,796 B1 | 3/2003 | Sauer et al. |
| 6,537,285 B1 | 3/2003 | Hatasaka, Jr. et al. |
| 6,551,315 B2 * | 4/2003 | Kortenbach et al. ........... 606/46 |
| 6,554,845 B1 | 4/2003 | Fleenor et al. |
| 6,558,400 B2 | 5/2003 | Deem et al. |
| 6,569,085 B2 | 5/2003 | Kotenbach et al. |
| 6,572,629 B2 | 6/2003 | Kalloo et al. |
| 6,595,984 B1 | 7/2003 | de Guillebon |
| 6,641,592 B1 | 11/2003 | Sauer et al. |
| 6,656,194 B1 | 12/2003 | Gannoe et al. |
| 6,663,639 B1 | 12/2003 | Laufer et al. |
| 6,689,051 B2 | 2/2004 | Nakada et al. |
| 6,695,764 B2 | 2/2004 | Silverman et al. |
| 6,716,232 B1 | 4/2004 | Vidal et al. |
| 6,719,763 B2 | 4/2004 | Chung et al. |
| 6,719,764 B1 | 4/2004 | Gellman et al. |
| 6,736,828 B1 | 5/2004 | Adams et al. |
| 6,746,460 B2 | 6/2004 | Gannoe et al. |
| 6,755,843 B2 | 6/2004 | Chung et al. |
| 6,761,685 B2 | 7/2004 | Adams et al. |
| 6,773,440 B2 | 8/2004 | Gannoe et al. |
| 6,773,441 B1 | 8/2004 | Laufer et al. |
| 6,821,285 B2 | 11/2004 | Laufer et al. |
| 6,835,199 B2 | 12/2004 | McGuckin, Jr. et al. |
| 7,112,208 B2 * | 9/2006 | Morris et al. ............... 606/144 |
| 7,316,703 B2 * | 1/2008 | Suzuki ...................... 606/208 |
| 2001/0016675 A1 | 8/2001 | Mortier et al. |
| 2001/0025171 A1 | 9/2001 | Mortier et al. |
| 2001/0049509 A1 | 12/2001 | Sekine et al. |
| 2001/0051815 A1 | 12/2001 | Esplin |
| 2001/0056282 A1 | 12/2001 | Sonnenschein et al. |
| 2002/0010490 A1 | 1/2002 | Schaller et al. |
| 2002/0013570 A1 | 1/2002 | Ruegg et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 | 4/2002 | Laufer et al. |
| 2002/0055757 A1 | 5/2002 | Torre et al. |
| 2002/0058855 A1 | 5/2002 | Schweich, Jr. et al. |
| 2002/0065534 A1 | 5/2002 | Hermann et al. |
| 2002/0068849 A1 | 6/2002 | Schweich, Jr. et al. |
| 2002/0068945 A1 | 6/2002 | Sixto, Jr. et al. |
| 2002/0072761 A1 | 6/2002 | Abrams et al. |
| 2002/0077524 A1 | 6/2002 | Schweich, Jr. et al. |
| 2002/0078967 A1 | 6/2002 | Sixto, Jr. et al. |
| 2002/0082621 A1 | 6/2002 | Schurr et al. |
| 2002/0082622 A1 | 6/2002 | Kane |
| 2002/0107530 A1 | 8/2002 | Sauer et al. |
| 2002/0183768 A1 | 12/2002 | Deem et al. |
| 2002/0193816 A1 | 12/2002 | Laufer et al. |
| 2003/0009085 A1 | 1/2003 | Arai et al. |
| 2003/0055442 A1 | 3/2003 | Laufer et al. |
| 2003/0065359 A1 | 4/2003 | Weller et al. |
| 2003/0109892 A1 | 6/2003 | Deem et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236536 A1 | 12/2003 | Grigoryants et al. |
| 2004/0010271 A1 | 1/2004 | Kortenbach |
| 2004/0030347 A1 | 2/2004 | Gannoe |
| 2004/0049095 A1 | 3/2004 | Goto et al. |
| 2004/0059346 A1 | 3/2004 | Adams et al. |
| 2004/0073089 A1 | 4/2004 | Nozue |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0122452 A1 | 6/2004 | Deem et al. |
| 2004/0122453 A1 | 6/2004 | Deem et al. |
| 2004/0122474 A1 | 6/2004 | Gellman et al. |
| 2004/0138682 A1 | 7/2004 | Onuki et al. |
| 2004/0147941 A1 | 7/2004 | Takemoto et al. |
| 2004/0176784 A1 | 9/2004 | Okada |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0215216 A1 | 10/2004 | Gannoe et al. |
| 2004/0243152 A1 | 12/2004 | Taylor et al. |
| 2004/0249362 A1 | 12/2004 | Levine et al. |
| 2004/0249392 A1 | 12/2004 | Mikkaichi et al. |
| 2004/0249395 A1 | 12/2004 | Mikkaichi et al. |
| 2005/0033320 A1 | 2/2005 | McGuckin, Jr. et al. |
| 2005/0033328 A1 | 2/2005 | Laufer et al. |
| 2005/0033354 A1 | 2/2005 | Montalvo et al. |
| 2005/0043758 A1 | 2/2005 | Golden et al. |
| 2005/0049617 A1 | 3/2005 | Chatlynne et al. |

FOREIGN PATENT DOCUMENTS

| | | |
|---|---|---|
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 97/12557 A1 | 4/1997 |
| WO | WO 99/22649 A2 | 5/1999 |
| WO | WO 99/65404 A1 | 12/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004542 A2 | 1/2004 |

| | | |
|---|---|---|
| WO | WO 2004/004542 A3 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/075787 A1 | 9/2004 |
| WO | WO 2004/084808 A2 | 10/2004 |
| WO | WO 2004/103189 A1 | 12/2004 |
| WO | WO 2005/004727 A1 | 1/2005 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, Jul. 1987, pp. 772-776.

Brolin et al., "Experimental Evaluation of Techniques of Gastric Paritioning for Morbid Obesity," *Surgery, Gynecology & Obstetrics*, vol. 153, Dec. 1981, pp. 878-882.

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.

Johnston et al. "The Magenstrasse and Mill Operation of Morbid Obesity", *Obesity Surgery* 13, 2003, pp. 10-16.

MICROLINE, 5mm. Reusable Graspers, [brochure], date unknown, 1 page.

MICROLINE, 5mm Scissors Tips [brochure], date unknown, 1 page.

MICROLINE, Dissector & Grasper Tips [brochure], date unknown, 1 page.

MICROLINE, Scissors Tips—5mm Monopolar Shears [brochure], date unknown, 1 page.

MICROLINE, Super-Atrau Disposable Laparoscopic Grasping Tips [Brochure], date unknown, 2 pages.

MICROLINE, The Microline Handpiece [brochure], date unknown, 1 page.

Okudaira et al., "The Healing and Tensile Strength of the Gastroplasty Staple Line," *The American Surgeon*, Oct. 1984, pp. 564-568.

Surgical Dynamics Inc., The S D sorb Meniscal Stapler [brochure] (1997), 3 pages total.

Sutura, The Next Generation in Vascular Suturing Devices: SuperStitch [brochure], date unknown, 2 pages total.

* cited by examiner

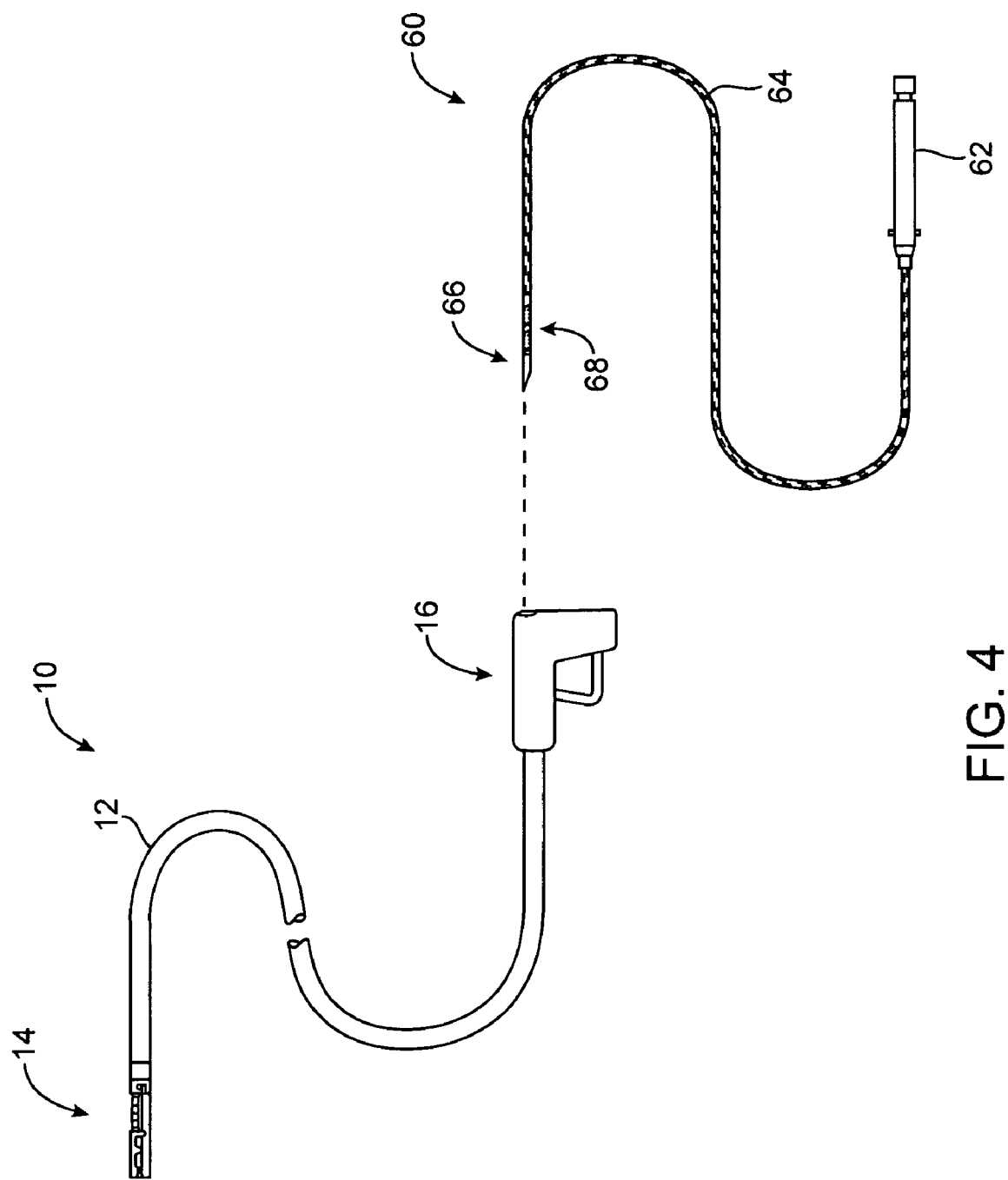

TISSUE MANIPULATION AND SECUREMENT SYSTEM

CROSS-REFERENCES TO RELATED APPLICATIONS

This application relates to, but does not claim priority from, the following: U.S. application Ser. No. 10/955,245, filed Sep. 29, 2004 now U.S. Pat. No. 7,347,863, U.S. application Ser. No. 10/840,950, filed May 7, 2004, and U.S. application Ser. No. 11/070,863, filed Mar. 1, 2005, each of which is incorporated herein by reference in its entirety.

BACKGROUND OF THE INVENTION

Field of the Invention. The present invention relates to methods and apparatus for manipulating and/or securing tissue. More particularly, the present invention relates to methods and apparatus for manipulating and/or securing tissue endoluminally, for instance, to form and/or secure tissue folds or to approximate regions of tissue, etc.

A number of surgical techniques have been developed to treat various gastrointestinal disorders. One such example of a pervasive disorder is morbid obesity. Conventional surgical treatment for morbid obesity typically includes, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in surgical procedures for gastrointestinal disorders typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen, for instance, includes four tissue layers, where the mucosa layer is the inner-most tissue layer followed by connective tissue, the muscularis layer, and where the serosa layer is the outer-most tissue layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intra-operatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., many of these devices are configured to be placed only after the tissue has been plicated and not during the actual plication procedure.

BRIEF SUMMARY OF THE INVENTION

An example of a tool which may be utilized for endoluminally accessing tissue may generally comprise a flexible catheter or tubular body which may be configured to be sufficiently flexible for advancement into a body lumen, e.g., transorally, percutaneously, laparoscopically, etc. The tubular body may be configured to be torqueable such that when a control handle is manipulated and/or rotated by a practitioner from outside the patient's body, the longitudinal and/or torquing force is transmitted along the flexible body such that the distal end of body is advanced, withdrawn, or rotated in a corresponding manner.

A tissue manipulation assembly may be located at the distal end of the tubular body and is generally used to contact and form tissue folds, as mentioned above. The tissue manipulation assembly may be connected to the distal end of the tubular body via a pivotable coupling and a lower jaw member may extend distally from the pivotable coupling with an upper jaw member, in this example, pivotably coupled to the lower jaw member via a jaw pivot. The location of the jaw pivot may be positioned at various locations along the lower jaw depending upon a number of factors, e.g., the desired size of the "bite" or opening for accepting tissue between the jaw members, the amount of closing force between the jaw members, etc. One or both jaw members may also have a number of protrusions, projections, grasping teeth, textured surfaces, etc., on the surface or surfaces of the jaw members to facilitate the adherence of tissue therebetween.

A launch tube may extend from the handle, through tubular body, and distally from the end of tubular body where a distal end of the launch tube is pivotally connected to the upper jaw member at a pivot. A distal portion of the launch tube may be pivoted into position within a channel or groove defined in upper jaw member to facilitate a low-profile configuration of the tissue manipulation assembly. When articulated, either via the launch tube or other mechanism, the jaw members may be urged into an open configuration to receive tissue in the jaw opening between the jaw members.

In operation, a shape-lockable endoscopic assembly may be advanced into a patient's stomach per-orally and through the esophagus. Such an endoscopic assembly may generally comprise an endoscopic device which may have a distal portion which may be articulated and steered to position its distal end anywhere within the stomach. Once desirably configured, the assembly may then be locked or rigidized to maintain its shape or configuration to allow for procedures to be performed on the tissue utilizing any number of tools delivered therethrough.

The tissue manipulation assembly may be delivered into the patient while in a low-profile configuration, e.g., transorally, through the shape-lockable endoscopic assembly, through an endoscope, an endoscopic device, or directly. Once desirably positioned, the launch tube may be urged proximally via its proximal end at handle. Because the jaw assembly pivot and the relative positioning of the upper jaw pivot along lower jaw member and launch tube pivot along upper jaw member, the proximal movement of the launch tube may effectively articulate upper jaw into an expanded jaw configuration. Proximally urging the launch tube may also urge the lower jaw member to pivot about the assembly pivot and form an angle relative to a longitudinal axis of the tubular body. The opening of the upper jaw relative to the lower jaw creates a jaw opening for grasping or receiving tissue. Moreover, the tissue manipulation assembly may also include a stop located adjacent to the jaw assembly pivot or within the pivot itself.

A second tool for initially engaging the tissue region of interest may also be deployed and utilized to engage the tissue and to position the engaged tissue between the jaws of the jaw assembly. Any number of tools may be used in combination with the tissue manipulation assembly. Once the tissue has been engaged between the jaw members, a needle assembly may be urged through the launch tube to pierce through the grasped tissue. Once the needle assembly has been passed through the engaged tissue, one or more tissue anchors may be deployed for securing the tissue.

BRIEF DESCRIPTION OF THE DRAWINGS

FIG. 4 shows an assembly view of how a needle deployment assembly may be introduced through a handle and tubular body of the tissue manipulation assembly.

DETAILED DESCRIPTION OF THE INVENTION

In manipulating tissue or creating tissue folds, a having a distal end effector may be advanced endoluminally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications may be seen in further detail in U.S. patent application Ser. No. 10/955,245 filed Sep. 29, 2004, which has been incorporated herein by reference above, as well as U.S. patent application Ser. No. 10/735,030 filed Dec. 12, 2003, which is incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

Figure 1A:
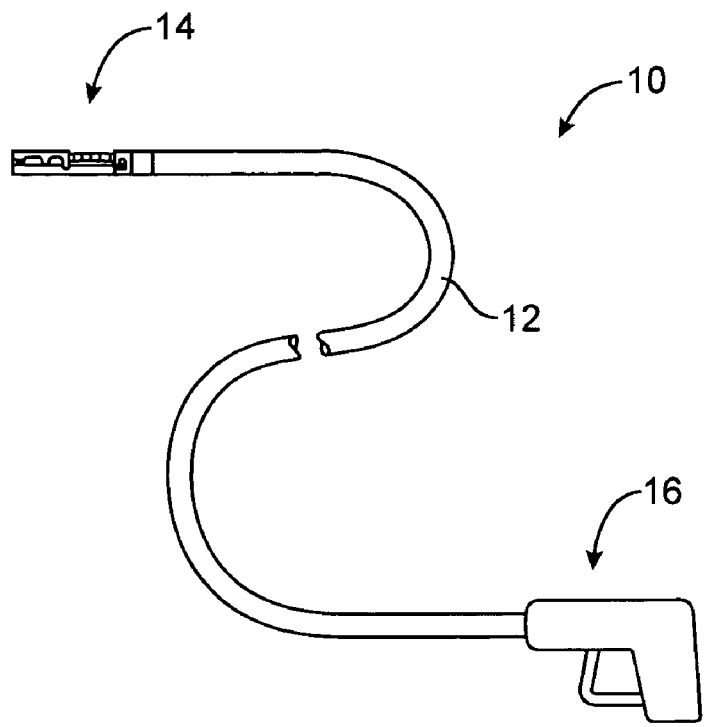
FIG. 1A shows a side view of one variation of a tissue manipulation assembly having a flexible body and a handle.

An illustrative side view of one example of a tool which may be utilized for endoluminally accessing tissue is shown in FIG. 1A, which shows assembly 10. The assembly 10 generally comprises a flexible catheter or tubular body 12 which may be configured to be sufficiently flexible for advancement into a body lumen, e.g., transorally, percutaneously, laparoscopically, etc. Tubular body 12 may be configured to be torqueable through various methods, e.g., utilizing a braided tubular construction, such that when handle 16 is manipulated and/or rotated by a practitioner from outside the patient's body, the longitudinal and/or torquing force is transmitted along body 12 such that the distal end of body 12 is advanced, withdrawn, or rotated in a corresponding manner.

Figure 1B:
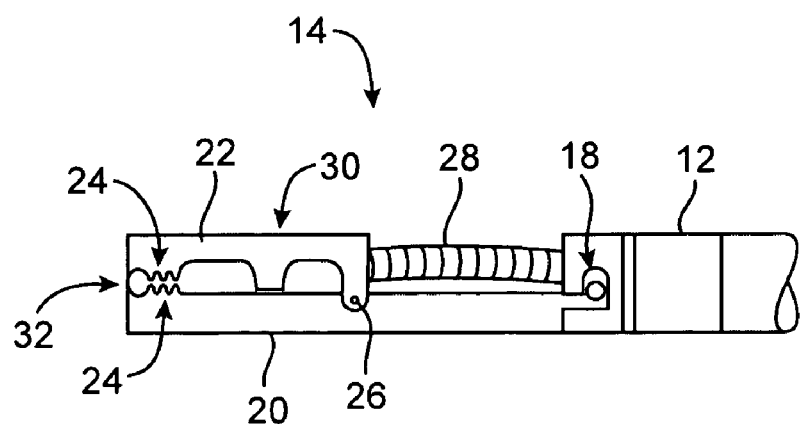
FIG. 1B illustrates a detail side view of a tissue manipulation assembly in a low-profile configuration connected to the distal end of the tubular body via a pivotable coupling.

Tissue manipulation assembly 14 is located at the distal end of tubular body 12 and is generally used to contact and form tissue folds, as mentioned above. FIG. 1B shows an illustrative detail side view in which tissue manipulation assembly 14 may be seen connected to the distal end of tubular body 12 via a pivotable coupling 18. Lower jaw member 20 extends distally from the pivotable coupling 18 and upper jaw member 22, in this example, may be pivotably coupled to lower jaw member 20 via jaw pivot 26. The location of jaw pivot 26 may be positioned at various locations along lower jaw 20 depending upon a number of factors, e.g., the desired size of the "bite" or opening for accepting tissue between the jaw members, the amount of closing force between the jaw members, etc. One or both jaw members 20, 22 may also have a number of protrusions, projections, grasping teeth, textured surfaces, etc., 24 on the surface or surfaces of the jaw members 20, 22 facing one another to facilitate the adherence of tissue between the jaw members 20, 22.

Launch tube 28 may extend from handle 16, through tubular body 12, and distally from the end of tubular body 12 where a distal end of launch tube 28 is pivotally connected to upper jaw member 22 at launch tube pivot 30. A distal portion of launch tube 28 may be pivoted into position within a channel or groove defined in upper jaw member 22, to facilitate a low-profile configuration of tissue manipulation assembly 14. When articulated, either via launch tube 28 or other mechanism, as described further below, jaw members 20, 22 may be urged into an open configuration to receive tissue in jaw opening 32 between the jaw members 20, 22.

Launch tube 28 may be advanced from its proximal end at handle 16 such that the portion of launch tube 28, which extends distally from body 12, is forced to rotate at hinge or pivot 30 and reconfigure itself such that the exposed portion forms a curved or arcuate shape that positions the launch tube opening perpendicularly relative to upper jaw member 22. Launch tube 28, or at least the exposed portion of launch tube 28, may be fabricated from a highly flexible material or it may be fabricated, e.g., from Nitinol tubing material which is adapted to flex, e.g., via circumferential slots, to permit bending.

Figure 2A:
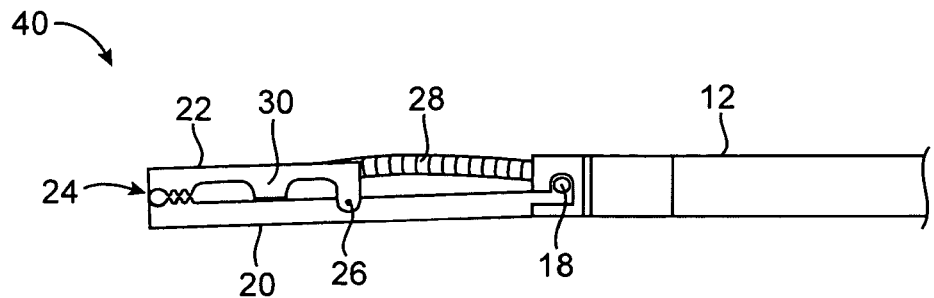
FIGS. 2A to 2C illustrate a method for articulating the tissue manipulation assembly from a low-profile configuration to an opened configuration and to a closed jaw configuration for clamping upon tissue, respectively.
Figure 2B:
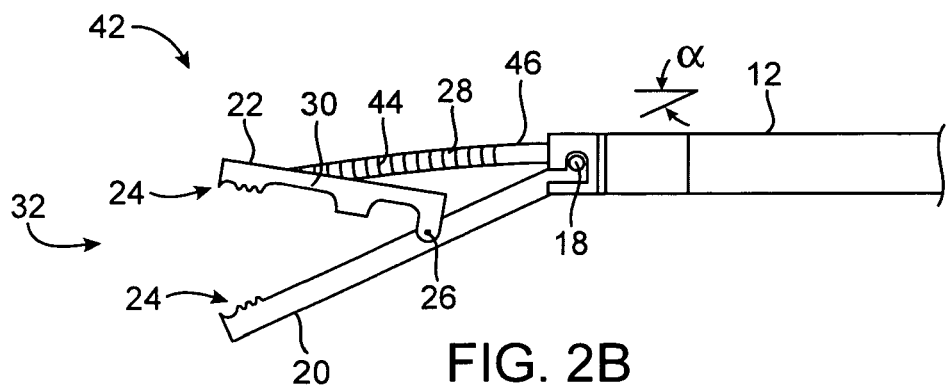
Figure 2C:
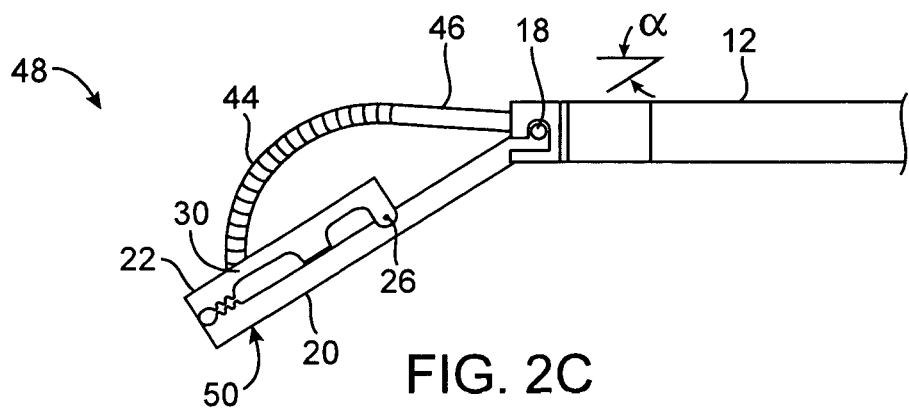

FIGS. 2A to 2C illustrate one method for articulating a tissue manipulation assembly into an opened and closed configuration. As shown in FIG. 2A, the assembly may be delivered into a patient while in a low-profile configuration 40, e.g., transorally, through an endoscope, an endoscopic device, or directly. Once desirably positioned, launch tube 28 may be urged proximally via its proximal end at handle 16. Because of jaw assembly pivot 18 and the relative positioning of upper jaw pivot 26 along lower jaw member 20 and launch tube pivot 30 along upper jaw member 22, the proximal movement of launch tube 28 may effectively articulate upper jaw 22 into an expanded jaw configuration 42, as shown in FIG. 2B. Proximally urging launch tube 28 may also urge lower jaw member 20 to pivot about assembly pivot 18 and form an angle, α, relative to a longitudinal axis of tubular body 12. The opening of upper jaw 22 relative to lower jaw 20 creates jaw opening 32 for grasping or receiving tissue. Moreover, the tissue manipulation assembly may also include a stop located adjacent to jaw assembly pivot 18 or within the pivot 18 itself.

Once launch tube 28 has been urged proximally, it may be locked into place thus locking the jaw configuration as well. Moreover, having the launch tube 28 articulate the jaw members 20, 22 in this variation eliminates the need for a separate jaw articulation and/or locking mechanism. Once the tissue has been pulled or manipulated between jaw members 20, 22, launch tube 28 may be pushed distally to actuate the jaw members 20, 22 into a closed, grasping configuration 48, as shown in FIG. 2C, for engagement with the tissue. As launch tube 28 is urged distally through body 12, lower jaw member 20 may be maintained at the angle, α, relative to the tissue to further facilitate manipulation of the grasped tissue.

Launch tube 28 may further define a flexible portion 44 distally of a rigid portion 46. Although launch tube 28 may be fabricated from different materials having differing flexibilities, it may also be fabricated from a single material, as mentioned above, where the flexible portion 44 may configured, e.g., by slotting, to allow for bending of the launch tube 28 in a plane to form a single curved or arcuate section while the rigid section 46 may extend at least partially into tubular body 12 to provide column strength to launch tube 28 while it is urged distally upon upper jaw member 22 and upon any tissue engaged thereby, as seen in the FIG. 2C.

Once the tissue has been engaged between jaw members 20, 22, a needle assembly may be urged through handle 16 and out through launch tube 28. The needle assembly may pass through lower jaw member 20 via needle assembly opening 50 defined in lower jaw member 20 to pierce through the grasped tissue. Once the needle assembly has been passed through the engaged tissue, one or more tissue anchors may be deployed for securing the tissue, as described in further detail in U.S. patent application Ser. No. 10/955,245, which has been incorporated by reference above.

Figure 3A:
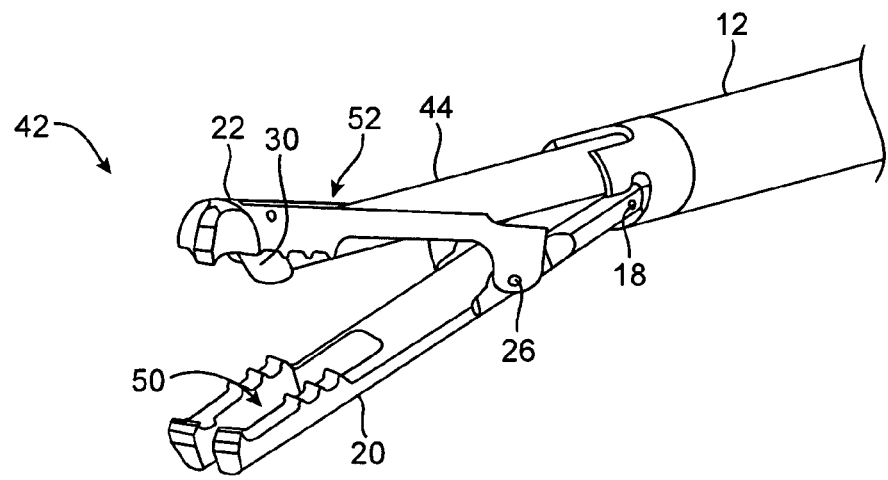
FIGS. 3A and 3B show detail perspective views of the tissue manipulation assembly in an open and clamped configuration, respectively.
Figure 3B:
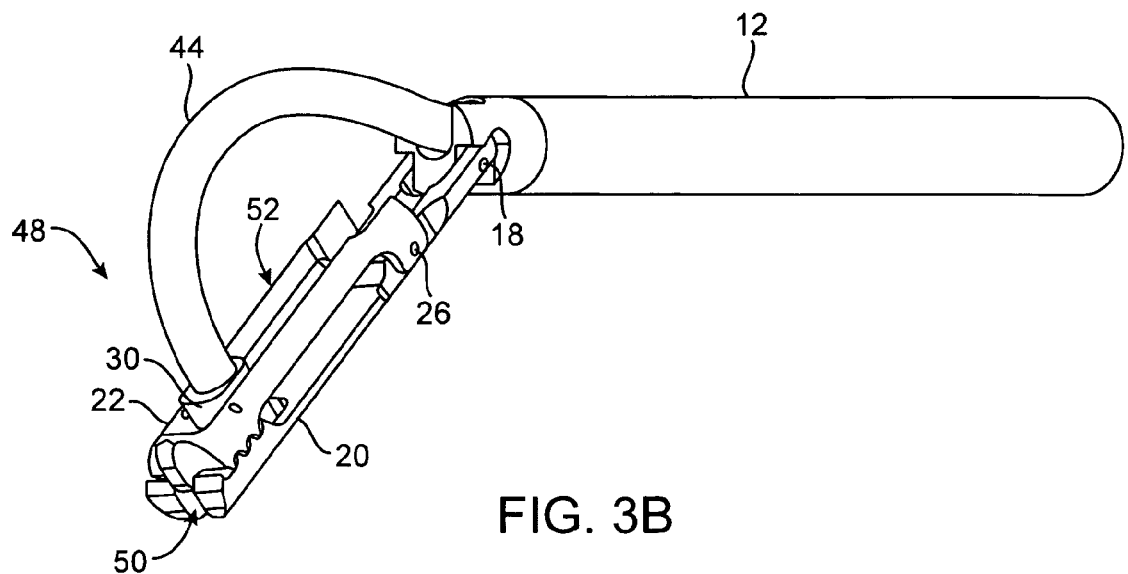

FIGS. 3A and 3B show detail perspective views of the tissue manipulation assembly. As shown in FIG. 3A, lower jaw member 20 and upper jaw member 22 may be seen its open configuration 42 when the launch tube has been urged proximally. Launch tube channel 52 may also be seen defined within upper jaw member 22 for providing a space for positioning the launch tube when in the low-profile configuration. Also shown is needle assembly opening 50 defined within lower jaw member 20 for passage of the needle assembly therethrough. FIG. 3B shows the assembly in its closed jaw configuration where the launch tube has been urged distally in which it rotates about launch tube pivot 30 such that the opening the launch tube become perpendicular relative to the jaw members 20, 22.

Although one particular variation of the jaw members 20, 22 is shown, this is not intended to be limiting in jaw member configuration or operation. Other variations may include various placement of the jaws relative to one another, alternative configurations for articulating the jaw members, alternative configurations for the launch tube placement, etc. Other variations are intended to be within the scope of this disclosure.

As mentioned above, a needle deployment assembly 60 may be deployed through the assembly 10 by introducing needle deployment assembly 60 into the handle 16 and through tubular body 12, as shown in the assembly view of FIG. 4, such that the needle assembly 66 is advanced from the launch tube and into or through approximated tissue. Once the needle assembly 66 has been advanced through the tissue, the anchor assembly 68 may be deployed or ejected. Anchor assembly 68 is normally positioned within the distal portion of tubular sheath 64 which extends from needle assembly control or housing 62. Once the anchor assembly 68 has been fully deployed from sheath 64, the spent needle deployment assembly 60 may be removed from assembly 10 and another needle deployment assembly may be introduced without having to remove assembly 10 from the patient. The length of sheath 64 is such that it may be passed entirely through the length of tubular body 12 to enable the deployment of needle assembly 66 into and/or through the tissue.

Figure 5A:
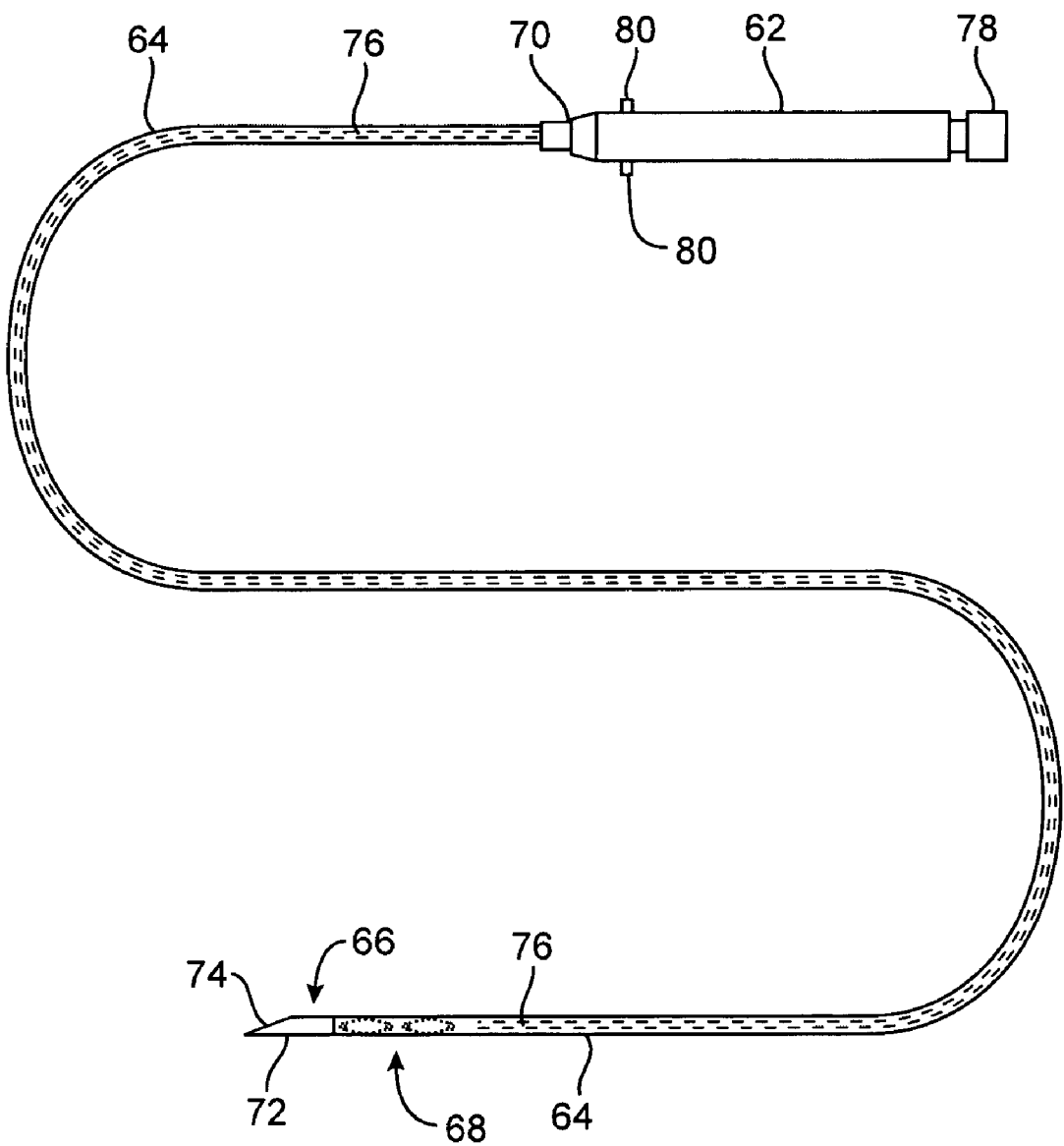
FIG. 5A shows a detailed assembly view of the needle deployment assembly from FIG. 4.

FIG. 5A shows a detailed assembly view of the needle deployment assembly 60 from FIG. 4. In this variation, elongate and flexible sheath or catheter 64 may extend removably from needle assembly control or housing 62. Sheath or catheter 64 and housing 62 may be interconnected via interlock 70 which may be adapted to allow for the securement as well as the rapid release of sheath 64 from housing 62 through any number of fastening methods, e.g., threaded connection, press-fit, releasable pin, etc. Needle body 72, which may be configured into any one of the variations described above, may extend from the distal end of sheath 64 while maintaining communication between the lumen of sheath 64 and needle opening 74.

Figure 5B:
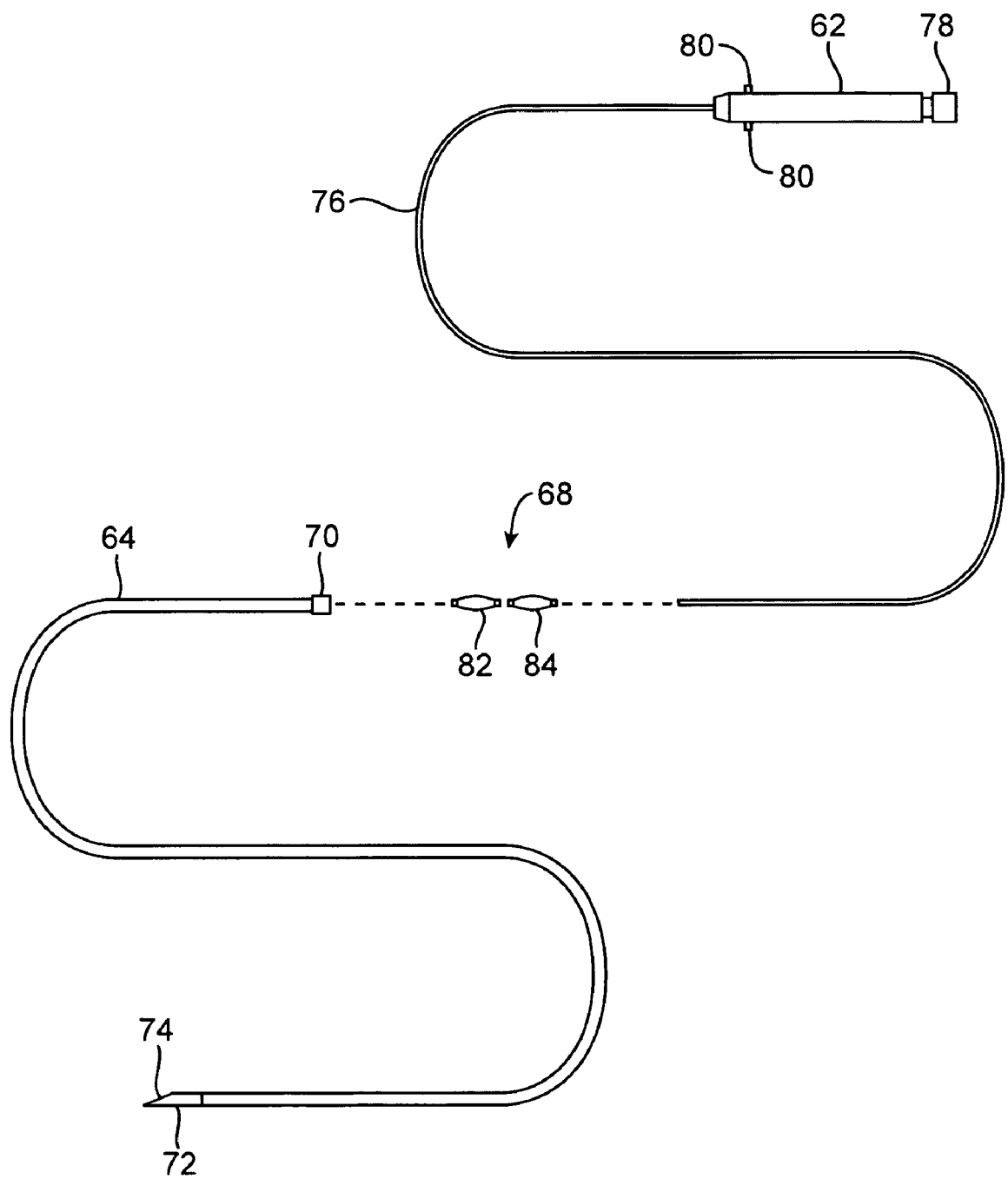
FIG. 5B shows an exploded assembly view of the needle deployment assembly from FIG. 5A.

Elongate pusher 76 may comprise a flexible wire or hypotube which is translationally disposed within sheath 64 and movably connected within housing 62. A proximally-located actuation member 78 may be rotatably or otherwise connected to housing 62 to selectively actuate the translational movement of elongate pusher 76 relative to sheath 64 for deploying the anchors from needle opening 74. Anchor assembly 68 may be seen positioned distally of elongate pusher 76 within sheath 64 for deployment from sheath 64. Needle assembly guides 80 may also be seen protruding from housing 62 for guidance through the locking mechanism described above. FIG. 5B shows an exploded assembly view of the needle deployment assembly 60 from FIG. 5A. As seen, sheath 64 may be disconnected from housing 62 via interlock 70 to reveal the elongate pusher 76 connected to housing 62 and the distal and proximal anchors 82, 84, respectively, of anchor assembly 68.

With respect to the anchor assemblies, the types of anchors shown and described are intended to be illustrative and are not limited to the variations shown. For instance, the tissue anchor variations may also include "T"-type anchors while other variations may include reconfigurable "basket"-type anchors, which may generally comprise a number of configurable struts or legs extending between at least two collars or support members or reconfigurable mesh structures extending between the two collars. Other variations of these or other types of anchors are also contemplated for use in an anchor assembly. Moreover, a single type of anchor may be used exclusively in an anchor assembly; alternatively, a combination of different anchor types may be used in an anchor assembly. Furthermore, the different types of cinching or locking mechanisms are not intended to be limited to any of the particular variations shown and described but may be utilized in any of the combinations or varying types of anchors as practicable.

Other variations for the needle assemblies and for the anchors are described in further detail in U.S. patent application Ser. No. 10/955,245, which has been incorporated by reference above.

In operation when manipulating and securing tissue within a patient's body, a separate elongate shaft having a tool on or near the distal end of the shaft may be utilized in conjunction with the tissue manipulation assembly 14. Such tools are generally utilized in endoluminal procedures where the tools are delivered through an endoscope. Generally, several different tools may be utilized for performing a procedure endoluminally.

Figure 6:
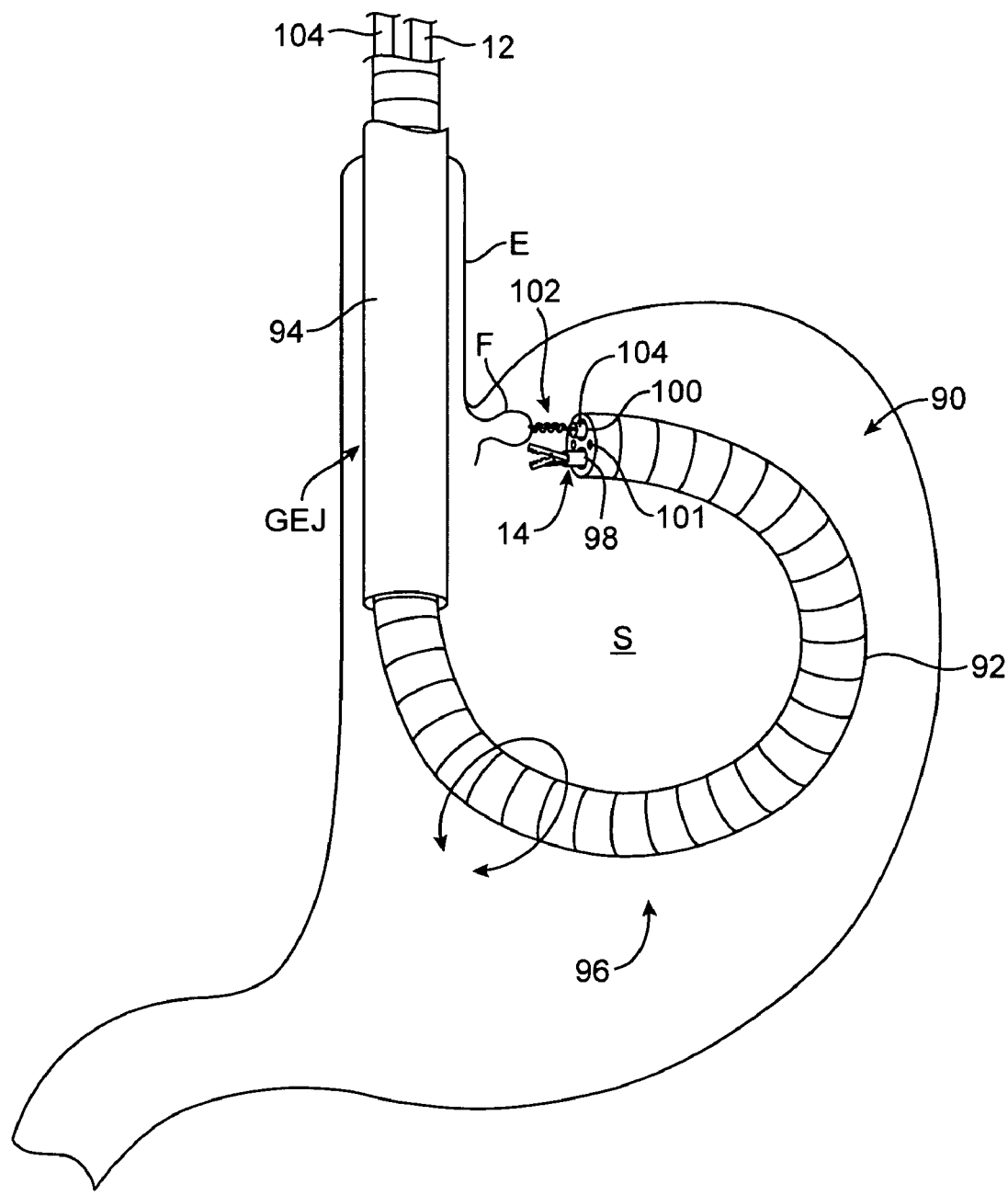
FIG. 6 illustrates one example in which a shape-lockable endoscopic assembly may be advanced into a patient's stomach per-orally and through the esophagus with a tissue manipulation assembly advanced through a first lumen and a tissue engagement member advanced through a second lumen.

As illustrated in FIG. 6, one such example is shown in which a shape-lockable endoscopic assembly 90 may be advanced into a patient's stomach S per-orally and through the esophagus E. Such an endoscopic assembly 90 may generally comprise an endoscopic device which may have a distal portion which may be articulated and steered to position its distal end anywhere within the stomach S. Once desirably configured, assembly 90 may then be locked or rigidized to maintain its shape or configuration to allow for procedures to be performed on the tissue utilizing any number of tools delivered through the assembly 90. Shape-lockable assembly 90 and its variations are described in further detail in U.S. patent application Ser. No. 10/734,562 filed Dec. 12, 2003, which is incorporated herein by reference in its entirety.

Shape-lockable assembly 90 may be generally comprised of shape-lockable endoscopic body 92 having an articulatable distal portion 96. The endoscopic body 92 may define at least first and second lumens 98, 100, respectively, through the endoscopic body 92 through which one or more tools may be deployed into the stomach S. Additional lumens may be provided through shape-lockable endoscopic body 92, such as a visualization lumen 101, through which an endoscope may be positioned to provide visualization of the region of tissue. Alternatively, an imager such as a CCD imager or optical fibers may be provided in lumen 101 to provide visualization. An optional thin wall sheath 94 may be disposed through the patient's mouth, esophagus E, and possibly past the gastroesophageal junction GEJ into the stomach S. Shape-lockable body 92 may be advanced through esophagus E (and through sheath 94, if utilized) and into stomach S while disposed in a flexible state.

Distal steerable portion 96 of endoscopic body 92 may be then articulated to an orientation, e.g., whereby distal portion 96 facilitates engagement of tissue near and/or inferior to the patient's gastroesophageal junction GEJ. Accordingly, distal steerable portion 96 may comprise a number of steering features, as described in further detail in U.S. patent application Ser. No. 10/734,562, incorporated above. With distal steerable portion 96 disposed in a desired configuration or orientation, endoscopic body 92 may be reversibly shape-locked to a rigid state such that the endoscopic body 92 maintains its position within the stomach S. Various methods and apparatus for rigidizing endoscopic body 92 along its length are also described in further detail in U.S. patent application Ser. No. 10/734,562, incorporated above.

FIG. 6 shows tissue manipulation assembly 14 having been advanced through first lumen 98 and a tissue engagement member 102 positioned upon flexible shaft 104 advanced through second lumen 100. As the tissue wall of a body lumen, such as the stomach, typically comprises an inner mucosal layer, connective tissue, the muscularis layer and the serosa layer. To obtain a durable purchase, e.g., in performing a stomach reduction procedure, tissue engagement member 102 may be advanced into contact with the tissue and preferably engages the tissue F such that when the tissue engagement member 102 is pulled proximally to draw the engaged tissue F between the jaw members 20, 22 of tissue manipulation assembly 14, at least the muscularis tissue layer and the serosa layer is drawn into tissue manipulation assembly 14.

Figure 7:
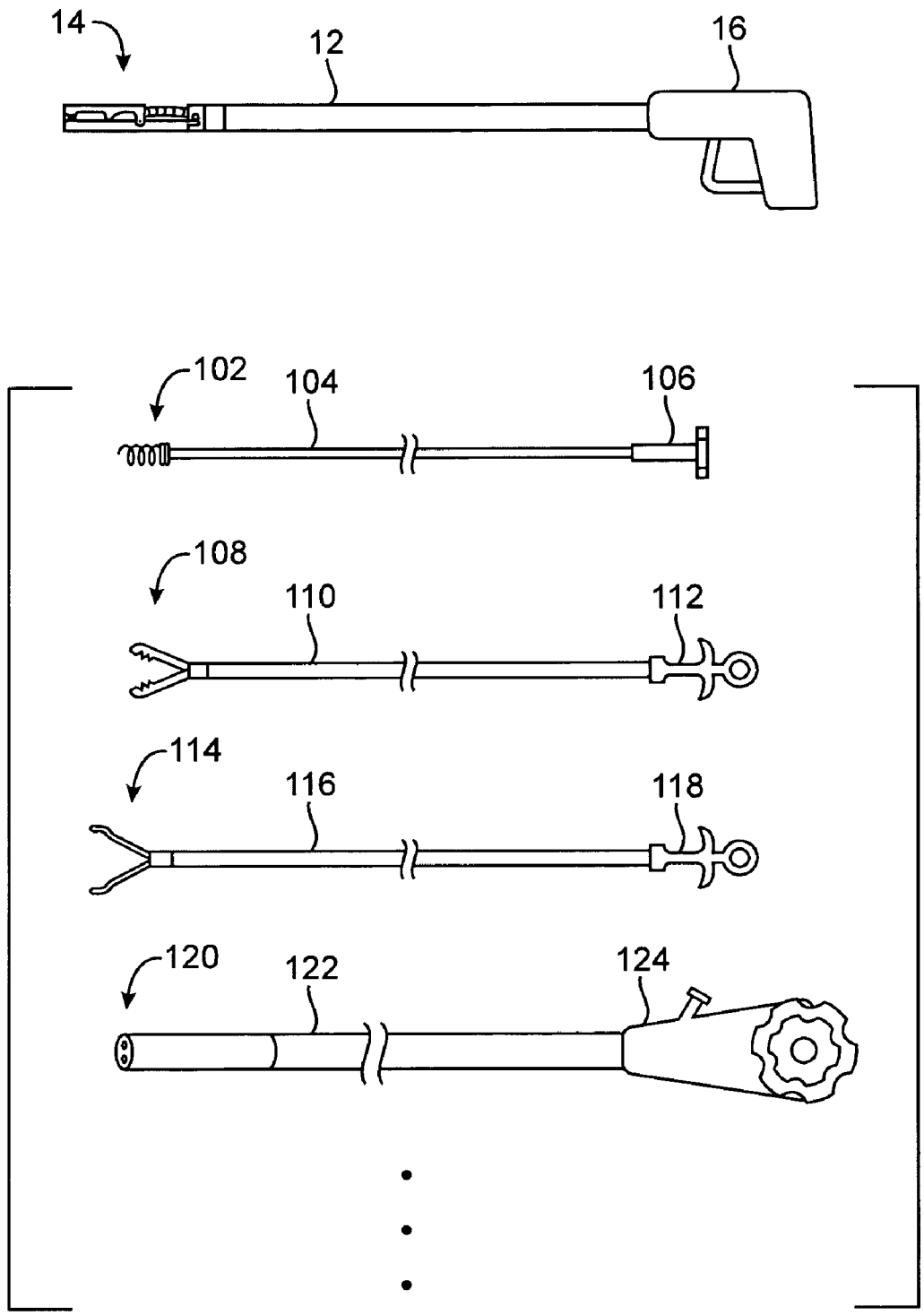
FIG. 7 illustrates a tissue manipulation assembly and examples of various tools which may be used in combination with the tissue manipulation assembly.

As tissue manipulation assembly 14 may be utilized to grasp and secure the engaged tissue, any number of tools may be utilized with tissue manipulation assembly 14, e.g., through shape-lockable endoscopic body 92, to engage and manipulate the tissue of interest relative to tissue manipulation assembly 14. FIG. 7 illustrates tissue manipulation assembly 14 upon flexible body 12 with handle 16 and examples of various tools which may be used in combination with tissue manipulation assembly 14.

Turning to FIG. 7, one example of a tool utilizable in combination with tissue manipulation assembly 14 is shown in tissue engagement member 102 as a tissue piercing helix or corkscrew structure upon flexible shaft 104 (as shown in FIG. 6). Tissue engagement member 102 may be rotated about its longitudinal axis to engage the tissue of interest by rotating handle 106 located on the proximal end of flexible shaft 104. Alternatively, a tool having aggressive tissue graspers 108 positioned upon flexible shaft 110 and articulatable via handle 112 may be utilized in combination with tissue manipulation assembly 14. Another alternative tool may be tissue graspers 114 positioned upon flexible shaft 116 and articulatable via handle 118. Tissue graspers 114 may have atraumatic grasping surfaces. In yet another alternative, an endoscope 122 having optical fibers or imager 120 may be utilized for providing visualization. Endoscope 122 may be articulated via handle 124 at its proximal end.

The examples of the various tools as shown and described are intended merely to be illustrative of the range of tools which may be usable with assembly 14 and are not intended to be limiting in any manner. Any number of other tools may be accordingly utilized and are intended to be within the scope of this disclosure.

Figure 8A:
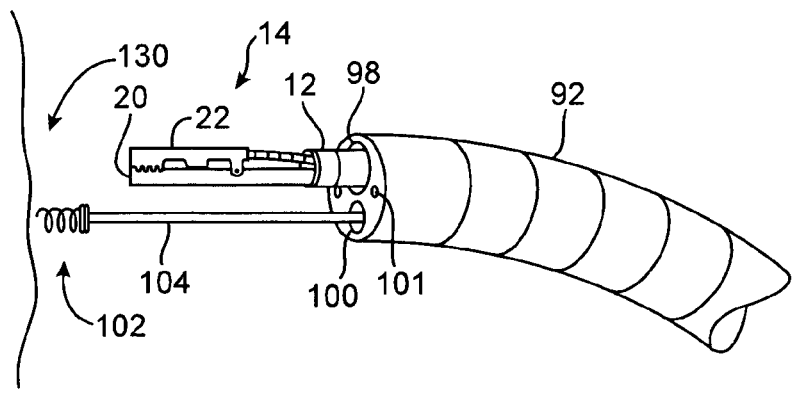
FIGS. 8A to 8D illustrate an example for performing an endoluminal tissue manipulation and securement procedure utilizing a tissue manipulation assembly in combination with a separate tissue grasping tool within, e.g., a patient's stomach.

An example of performing an endoluminal tissue manipulation and securement procedure utilizing tissue manipulation assembly 14 in combination with a separate tissue grasping tool within, e.g., a patient's stomach, is illustrated in FIGS. 8A to 8D. As shown in FIG. 8A, once shape-lockable endoscopic body 92 has been introduced into the patient, e.g., trans-orally, trans-anally, percutaneously, etc., and desirably positioned relative to a tissue region of interest 130, endoscopic body 92 may be rigidized to maintain its configuration within the patient body. Alternatively, it may be left in a flexible state during the procedure.

Figure 8B:
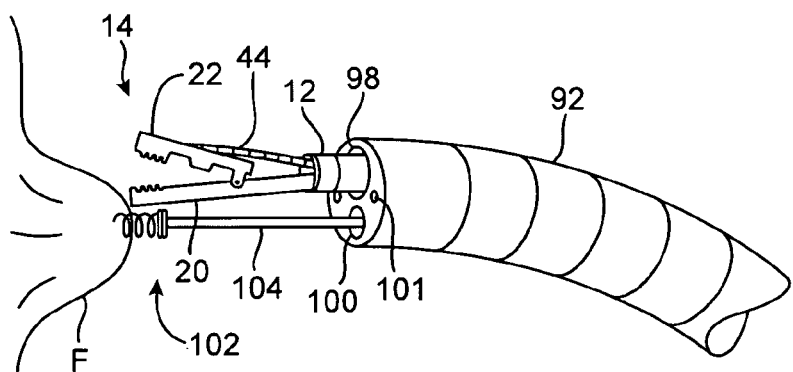

The tissue region of interest 130 as well as the procedure may be visualized through visualization lumen 101 or a separate imager, as described above. In either case, tissue manipulation assembly 14 and tissue engagement member 102 may be advanced distally out from endoscopic body 92 through their respective lumens 98, 100. Tissue engagement member 102 may be advanced into contact against the tissue surface, as shown in FIG. 8A, and then rotated via its proximal handle until the tissue is engaged. The engaged tissue F may be pulled proximally relative to endoscopic body 92 and tissue manipulation assembly 14 may be actuated via its proximally located handle into an open expanded jaw configuration for receiving the engaged tissue F, as shown in FIG. 8B.

Alternatively, once the tissue F has been engaged, tissue manipulation assembly 14 may be advanced distally in its open configuration onto the engaged tissue. In yet another variation, tissue engagement member 102 may be omitted entirely and tissue manipulation assembly 14 may be utilized alone to grasp onto the tissue region of interest 130. In yet another alternative, a second tissue manipulation assembly may be used in combination with tissue manipulation assembly 14.

Figure 8C:
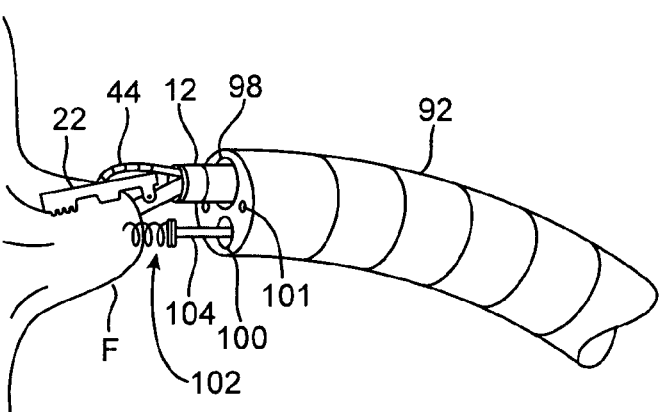

Turning back to FIG. 8B, tissue manipulation assembly 14 may be articulated to receive the engaged tissue F. As shown in FIG. 8C, once engaged tissue F is positioned between jaw members 20, 22, the launch tube may be urged proximally to actuate upper jaw member 22 to grasp or clamp upon the tissue F. Tissue engagement member 102 may be retracted from the tissue F or it may be left within the tissue while tissue manipulation assembly engages and secures the tissue F.

Figure 8D:
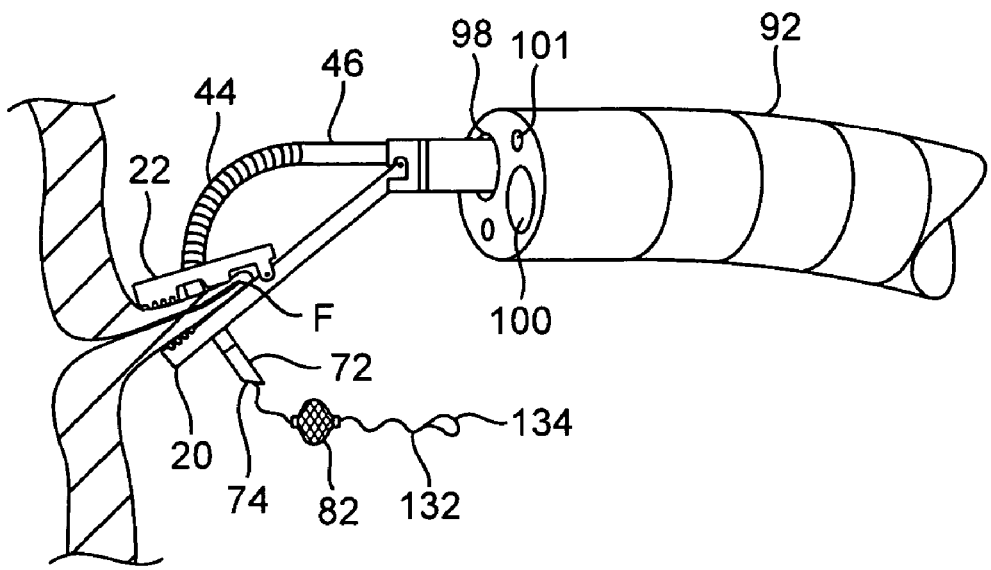

FIG. 8D shows a partial cross-sectional view of the tissue F while engaged to tissue manipulation assembly 14. Tissue engagement member 102 has been omitted from this view only for the sake of clarity. As mentioned above, member 102 may be left remaining in the tissue F, disengaged from tissue F, or disengaged and removed entirely from endoscopic body 92, if so desired, and another tool may be advanced through lumen 100 to facilitate the procedure. Once jaw members 20, 22 have been actuated to clamp or grasp upon tissue F by the launch tube, the launch tube may be automatically positioned into its anchor deployment configuration. The needle assembly may then be urged via manipulation from its proximal end at handle 16 through the launch tube to pierce preferably through a dual serosa layer through engaged tissue F and past lower jaw member 20. As described above, the engaged tissue F positioned between the jaw members 20, 22 is desirably engaged such that the needle body 72, when urged through the tissue F, is disposed through the muscularis and/or serosa layers of the engaged tissue F. Once needle body 72 has passed through tissue F, one or more expandable tissue anchors may be ejected from needle body 72 through needle opening 74.

Because needle body 72 may penetrate the tissue wall twice, it exits within the body lumen if utilized within, e.g., the stomach, thus reducing the potential for injury to surrounding organs. As described above, needle body 72 may define needle lumen or opening 74 through which expandable an anchor, e.g., distal anchor 82 and/or proximal anchor 84, may be situated during deployment and positioning of the assembly. A single suture or flexible element 132 (or multiple suture elements) may connect distal anchor 82 and proximal anchor 84 to one another and end in terminal loop 134. For instance, element 132 may comprise various materials such as monofilament, multifilament, or any other conventional suture material, elastic or elastomeric materials, e.g., rubber, etc.

Once distal anchor 82 has been ejected, needle body 72 may be urged proximally back through tissue F, where proximal anchor 84 may then be ejected from needle body 72 with suture 132 still connecting the two anchors 82, 84 through tissue F. Alternatively, tissue manipulation assembly 14, with suture 132 still depending therefrom, may be disengaged from tissue F and the procedure may be repeated at a second region of tissue where proximal anchor 84 may then be ejected.

Figure 9A:
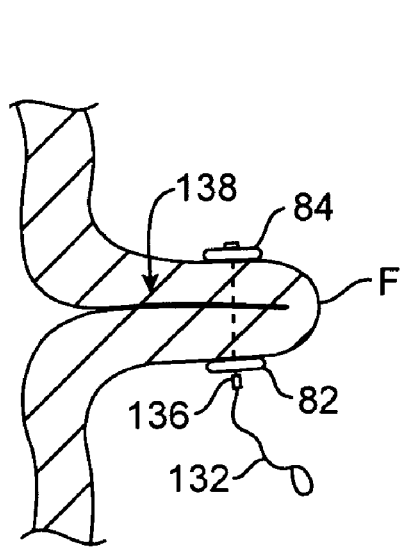
FIG. 9A shows one variation where a single tissue fold may be secured between tissue anchors using the tissue manipulation assembly.

FIG. 9A shows one variation where a single fold F may be secured between proximal anchor 82 and distal anchor 84. With both anchors 82, 84 disposed externally of the launch tube and suture 132 connecting the two, proximal anchor 84 may be urged into contact against tissue F. As the anchors are urged against tissue fold F, distal anchor 82 or a portion of suture 132 may be configured to provide any number of directionally translatable locking mechanisms 136 which provide for movement of an anchor along suture 132 in a first direction and preferably locks, inhibits, or prevents the reverse movement of the anchor back along suture 132.

Figure 9B:
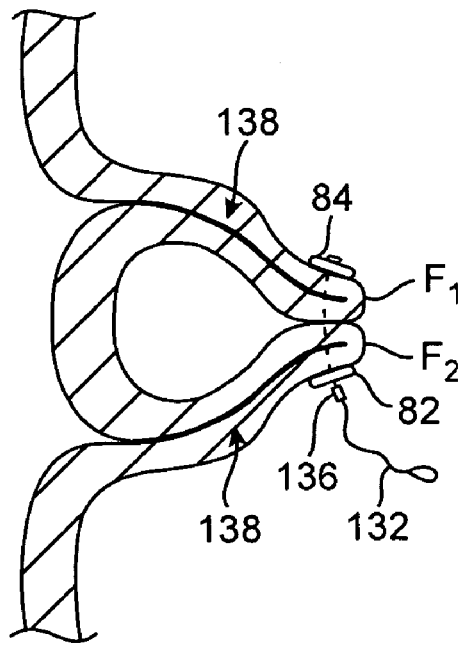
FIG. 9B shows another variation where two or more tissue folds may be secured between tissue anchors using the tissue manipulation assembly.

FIG. 9B shows another variation where a at least two folds $F_1$ and $F_2$ may be secured between proximal anchor 82 and distal anchor 84. After the anchors have been ejected from needle body 72, the anchors may be approximated towards one another over suture 132 thus bringing folds $F_1$ and $F_2$ towards one another. Although a single tissue fold and a dual fold are shown in these examples, any number of folds or tissue ridges may be created using the tools disclosed herein. Moreover, these examples are merely intended to be illustrative and not limiting in any way. In either case, it may be generally desirable to form the tissue folds such that serosa-to-serosa contact 138 occurs between the layers of secured tissue, although this may not be necessary.

Various examples of cinching devices and methods which may be utilized with the tools and devices herein are described in further detail in U.S. patent application Ser. No. 10/840,950 filed May 7, 2004, which has been incorporated herein above.

Figure 10A:
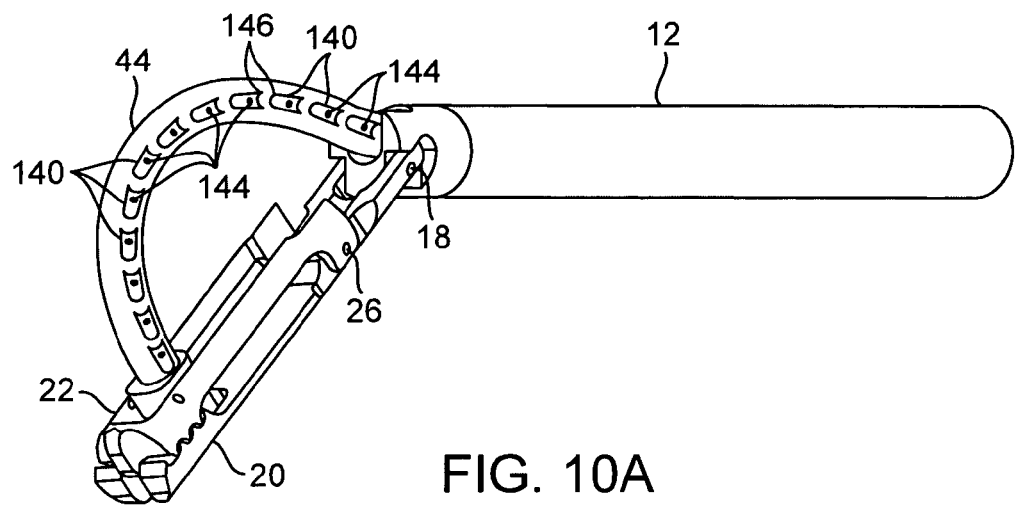
FIGS. 10A and 10B illustrate a variation of the tissue manipulation assembly in a perspective and cross-sectional view, respectively, where a number of reinforcement members or bars may be positioned along the launch tube to increase its column strength.
Figure 10B:
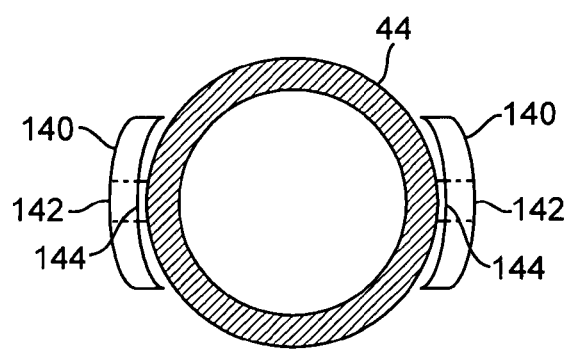

In using the launch tube as a jaw actuation mechanism, other variations of the launch tube may be utilized to ensure sufficient strength and force transmission in tissue manipulation assembly 14 for jaw member actuation. One such example is shown in the perspective view of FIG. 10A, which shows launch tube 44 having a number of reinforcement members or bars 140 aligned along one or both sides of the launch tube to provide for additional column strength. Each of the reinforcement members 140 may be pivotally attached to launch tube 44 via pivot members 144 rotatably secured within pivot channels 142, as seen in the launch tube cross-section in FIG. 10B. Moreover, each of the pivot members 144 may define cooperating adjacent members relative to one another while maintaining contact to allow for the transmission of force between the members 144. Pivot members 144 may be positioned along the length of the exposed launch tube or a portion of the launch tube; moreover, a single side of the launch tube may have pivot members 144 attached thereto. Alternatively, rather than utilizing pivot members, portions of the launch tube itself may be simply thickened to increase its column strength and force transmission capabilities.

Figure 11A:
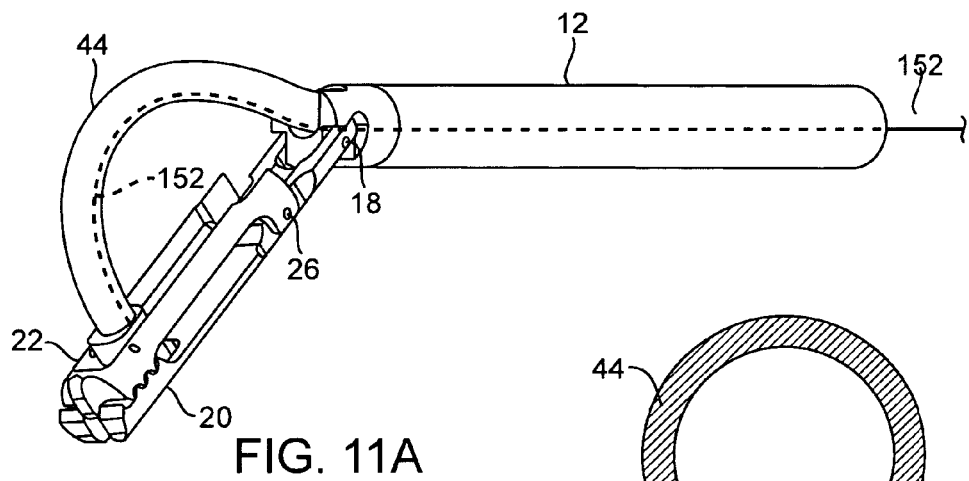
FIGS. 11A and 11B illustrate another variation of the tissue manipulation assembly in a perspective and cross-sectional view, respectively, where a pull wire may be routed through the launch tube to facilitate articulation of the launch tube and/or jaw assembly.
Figure 11B:
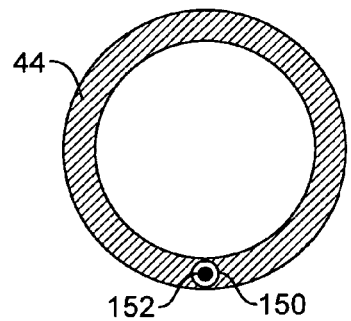
Figure 12:
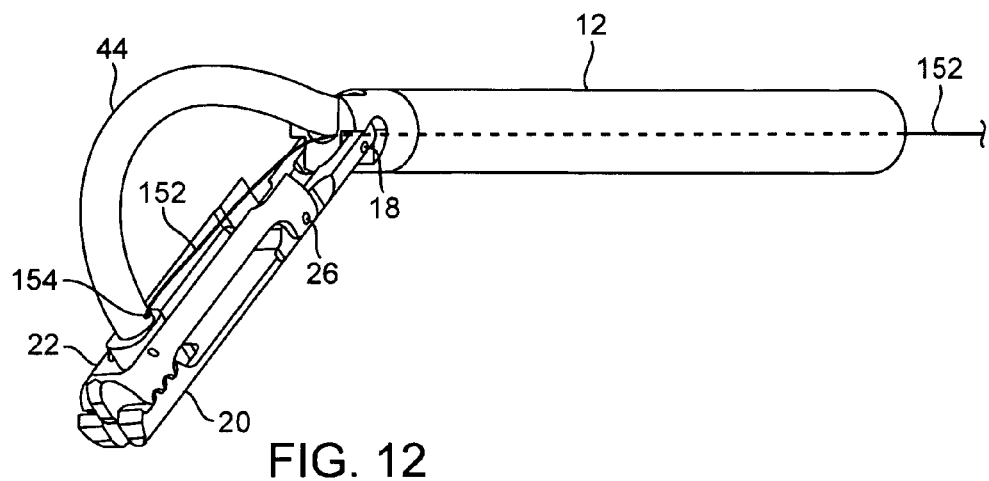
FIG. 12 illustrates yet another variation of the tissue manipulate assembly which may also utilize a pull wire connected directly to the launch tube.

In another variation, as shown in FIG. 11A and the launch tube cross-section in FIG. 11B, a pull wire 152 may be routed through tubular body 12 and launch tube 44 through a pull wire lumen 150 to provide a launch tube and jaw actuation mechanism separate from the launch tube actuation itself. Pull wire 152 may be manipulated via its proximal end at handle 16 by pulling or pushing pull wire 152 to actuate launch tube 44 and/or jaw members 20, 22. Alternatively, pull wire 152 may be routed through tubular body 12 and connected directly to launch tube 44 at pull wire attachment point 154 rather than routing it through the launch tube. Again, manipulation of pull wire 152 may be utilized to articulate the launch tube configuration as well as jaw member articulation.

Although a number of illustrative variations are described above, it will be apparent to those skilled in the art that various changes and modifications may be made thereto without departing from the scope of the invention. Moreover, although specific configurations and applications may be shown, it is intended that the various features may be utilized in various combinations and in various types of procedures as practicable. It is intended in the appended claims to cover all such changes and modifications that fall within the true spirit and scope of the invention.

What is claimed is:

1. A tissue securement apparatus, comprising:
   an elongate body having a proximal end, a distal end, and a flexible length therebetween;
   a first jaw member pivotably coupled to the distal end of the elongate member such that the first jaw pivots around a first pivot axis;
   a second jaw member pivotably coupled to the first jaw member such that the second jaw pivots around a second pivot axis that does not coincide with the first pivot axis;
   a launch tube defining a lumen therethrough, the launch tube being slidably positioned along the elongate body and pivotably coupled to the second jaw member; and
   an anchor assembly and anchor deployment catheter movably positioned within the launch tube.

2. The apparatus of claim 1 wherein at least one of the first and second jaw members comprise protrusions for facilitating engagement onto the tissue.

3. The apparatus of claim 1, wherein the lumen of said launch tube extends to the distal end of the launch tube, and wherein a distal end of the launch tube is pivotably coupled to the second jaw member.

4. The apparatus of claim 1 wherein the launch tube comprises a distally located flexible portion.

5. The apparatus of claim 4 wherein the launch tube further comprises a rigid portion proximally of the flexible portion.

6. The apparatus of claim 1 wherein the first and second jaw members are adapted to configure into an expanded configuration when the launch tube is urged proximally.

7. The apparatus of claim 1 wherein the first and second jaw members are adapted to configure into a grasping configuration when the launch tube is urged distally.

8. The apparatus of claim 1 wherein the first jaw member defines an opening for passage of a needle assembly therethrough.

9. The apparatus of claim 1 wherein said anchor deployment catheter comprises a needle assembly slidably positioned within the launch tube, the needle assembly having a needle body and a flexible sheath, with said anchor assembly being positioned within a distal portion of the flexible sheath.

10. The apparatus of claim 1, wherein said anchor assembly comprises a distal anchor, a proximal anchor, and a connector that connects the distal anchor to the proximal anchor.

11. A tissue securement apparatus, comprising:
    an elongate body having a proximal end, a distal end, and defining a first lumen that extends through at least a portion of the elongate body, the elongate body further defining a longitudinal axis;
    a first jaw member pivotably coupled to the elongate member at or near its distal end;
    a second jaw member pivotably coupled to the first jaw member;
    a launch tube defining a second lumen therethrough, the launch tube having a proximal portion that is substantially coaxial with and movably positioned within the first lumen of the elongate body, the launch tube also having a distal portion that is pivotably coupled to the second jaw member; and
    an anchor assembly and anchor deployment catheter movably positioned within the launch tube.

12. The apparatus of claim 11, wherein said launch tube distal portion extends from a distal end of the first lumen, the distal portion of the launch tube having a first position in which it is substantially coaxial with the elongate body, and a second position in which it has a substantially arcuate shape and is not coaxial with the elongate body.

13. The apparatus of claim 12, wherein the distal portion of said launch tube is substantially restricted to a single plane.

14. The apparatus of claim 11, wherein said launch tube distal portion includes circumferential slots to permit bending of the distal portion.

15. The apparatus of claim 11, wherein movement of said launch tube relative to said elongate body causes pivoting motion of said first jaw member and said second jaw member.

16. The apparatus of claim 15, wherein said launch tube has:
    a first position relative to said elongate body that corresponds with a low-profile configuration of said first jaw member and said second jaw member,
    a second position relative to said elongate body that corresponds with an expanded configuration of said first jaw member and said second jaw member, and
    a third position relative to said elongate body that corresponds with a grasping configuration of said first jaw member and said second jaw member.

17. The apparatus of claim 16, wherein said second position of said launch tube is distal of said first position, and wherein said third position of said launch tube is distal of said second position.

18. The apparatus of claim 16, wherein said launch tube distal portion extends from a distal end of the first lumen, the distal portion of the launch tube having a substantially arcuate shape when said launch tube is in the third position relative to the elongate body.

19. The apparatus of claim 11, wherein said anchor deployment catheter comprises a needle assembly slidably positioned within the second lumen, the needle assembly having a needle body and a flexible sheath, with said anchor assembly being positioned within a distal portion of the flexible sheath.

20. The apparatus of claim 19, wherein said anchor assembly comprises a distal anchor, a proximal anchor, and a connector that connects the distal anchor to the proximal anchor.

21. The apparatus of claim 11, wherein the second lumen extends to the distal portion of the launch tube.

* * * * *